(12) United States Patent
Lucke et al.

(10) Patent No.: US 8,940,248 B2
(45) Date of Patent: Jan. 27, 2015

(54) KIT

(71) Applicant: Eppendorf, Hamburg (DE)

(72) Inventors: Judith Lucke, Hamburg (DE);
Jens-Peter Kroog, Großhansdorf (DE);
Helmut Knofe, Norderstedt (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 13/872,589

(22) Filed: Apr. 29, 2013

(65) Prior Publication Data

US 2013/0344614 A1 Dec. 26, 2013

Related U.S. Application Data

(60) Provisional application No. 61/639,240, filed on Apr. 27, 2012.

(30) Foreign Application Priority Data

Apr. 27, 2012 (EP) ..................................... 12002984

(51) Int. Cl.
| | | |
|---|---|---|
| *B01L 3/00* | (2006.01) | |
| *G01N 35/10* | (2006.01) | |
| *B01L 9/00* | (2006.01) | |
| *B01L 9/06* | (2006.01) | |
| *B65B 5/06* | (2006.01) | |

(52) U.S. Cl.
CPC . *G01N 35/10* (2013.01); *B01L 3/52* (2013.01); *B01L 9/00* (2013.01); *B01L 9/06* (2013.01); *B65B 5/06* (2013.01); *B01L 2200/16* (2013.01); *B01L 2200/18* (2013.01); *B01L 2300/042* (2013.01); *B01L 2300/0609* (2013.01); *B01L 2300/0809* (2013.01); *Y10S 436/815* (2013.01); *Y10S 436/817* (2013.01)
USPC .......... 422/430; 422/400; 422/401; 422/408; 422/500; 422/547; 422/549; 422/550; 422/552; 422/554; 422/556; 422/557; 422/558; 422/559; 422/560; 422/561; 422/562; 422/939; 422/940; 436/164; 436/165; 436/169; 436/170; 436/174; 436/815; 436/817

(58) Field of Classification Search
USPC ......... 422/400, 401, 408, 430, 500, 547, 549, 422/550, 552, 554, 556, 557, 558, 559, 560, 422/561, 562, 939, 940; 436/164, 165, 169, 436/170, 174, 815, 817
See application file for complete search history.

(56) References Cited

U.S. PATENT DOCUMENTS

2005/0265901 A1   12/2005   Sinclair et al.

FOREIGN PATENT DOCUMENTS

| DE | 20216693 | 2/2003 |
|---|---|---|
| GB | 2472252 | 2/2011 |
| WO | 2007/121324 | 10/2007 |
| WO | 2008/003338 | 1/2008 |

*Primary Examiner* — Dennis M White
(74) *Attorney, Agent, or Firm* — Vidas, Arrett & Steinkraus, P.A.

(57) ABSTRACT

A kit comprising a carrier and vessels arranged on the carrier, wherein different reagents are contained in different vessels, the vessels are arranged with an openable closing device on top of the carrier, the carrier has a footprint on the bottom side for being placed on a base, and the carrier has bottom positioning means for being positioned on at least one workplace of an automated laboratory system for microtiter plates according to the SBS standard.

21 Claims, 14 Drawing Sheets

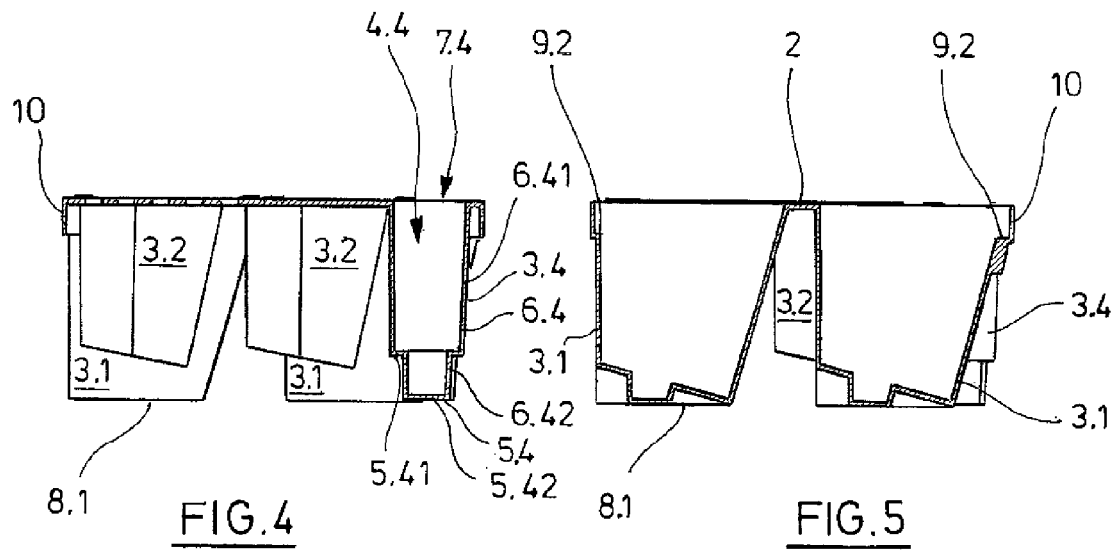
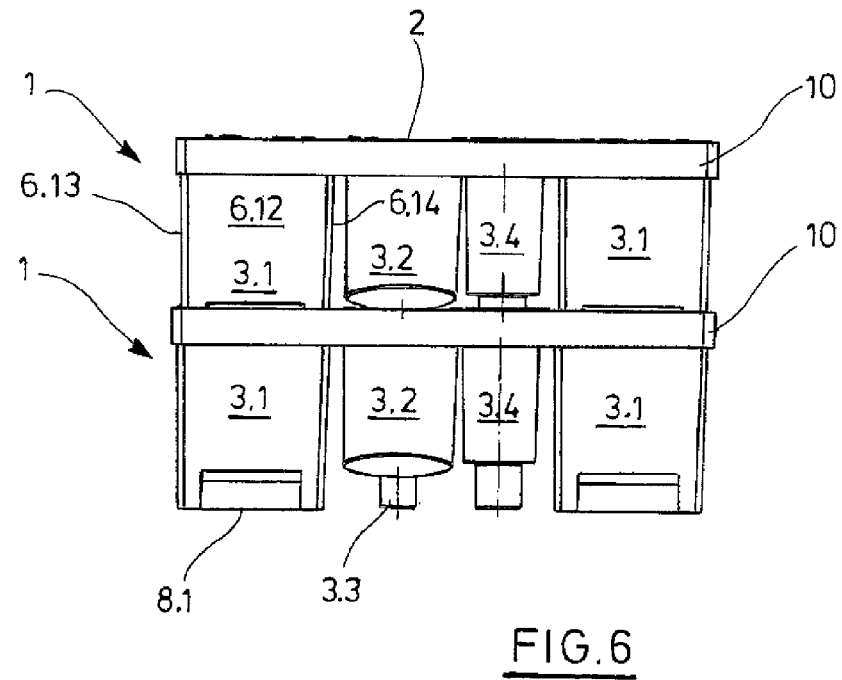

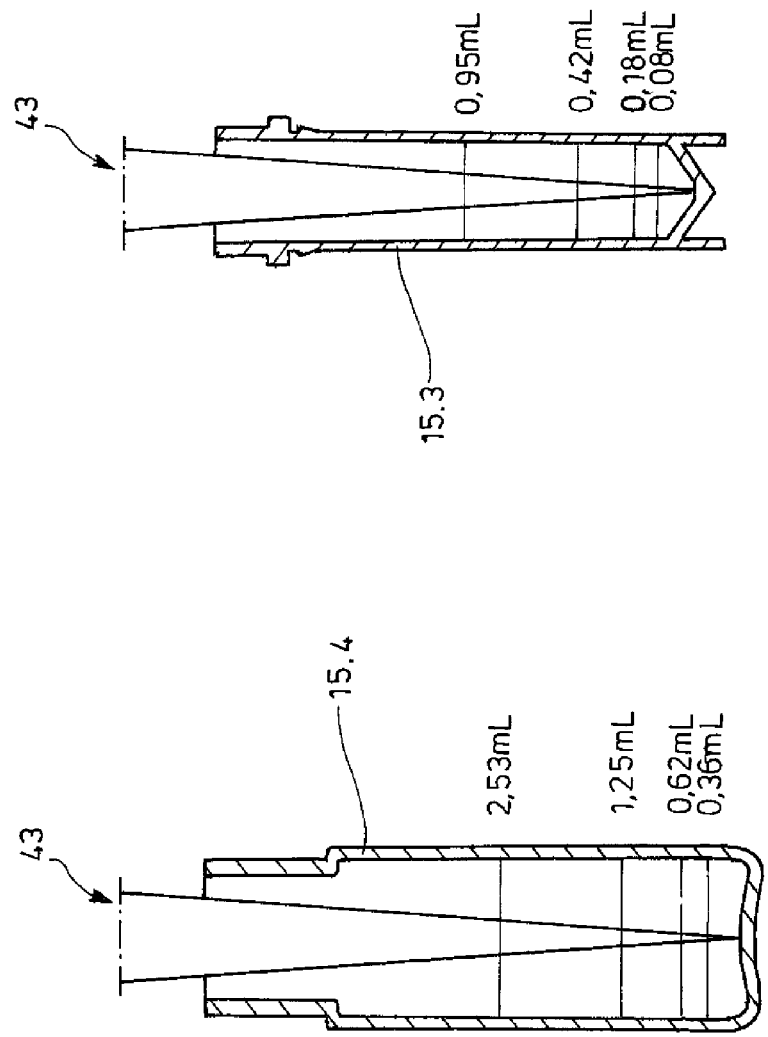

KIT

CROSS-REFERENCE TO RELATED APPLICATIONS

Not applicable

STATEMENT REGARDING FEDERALLY SPONSORED RESEARCH

Not applicable

BACKGROUND OF THE INVENTION

The invention relates to a kit comprising various reagents in various vessels.

To perform numerous procedures with automated laboratory systems (workstations) in chemical, biochemical, biological, medical or forensic laboratories, reagents are required that can be used to prepare samples for analysis. One example of this is the purification of nucleic acids with the assistance of magnetic particles. Nucleic acids are repeatedly dissolved in special reagents, attached to magnetic particles, and then separated from the reagents.

In conventional methods, the reagents are generally placed manually on the work surface of the automated laboratory system. The reagents themselves are generally delivered in the form of an unorganized collection of sealed vessels enclosed in a plastic bag in a folding box made of cardboard. The user must open the vessels and place them in designated holding device (racks) at a predetermined position on the work surface. This ensures that the automated laboratory system accesses the correct reagent while the method is being automatically performed. The controls of the automated laboratory system naturally assume that the necessary reagents are provided at the designated positions on the work surface. In certain cases, the user must pour the contents of the individual reagent vessels into special system vessels that are recognized by the controls of the automated laboratory system.

WO 2008/003338 A, the entire contents of which is incorporated herein by reference, describes a modular storage system for laboratory fluids with a support frame having a specific number of slots for at least two different laboratory vessel inserts that can be exchanged as desired and inserted into the slots of the support frame combined as desired in a form-fitting manner, and that each have at least one laboratory vessel and/or at least one compartment for at least one laboratory vessel.

It is time-consuming to place the vessels with the required reagents at the predetermined positions. This increases the danger of confusion. A collection of vessels can easily occur when the remaining reagents are in intermediate storage in refrigerators. This can give rise to confusion, for example, when vessels with different opening dates are confused. The user must therefore spend a lot of time organizing.

Another disadvantage is that reagent residue frequently remains in the vessels which cannot be removed by the automated laboratory system with a pipette or other dosing device. The user frequently needs to add more reagents, and this also increases costs.

BRIEF SUMMARY OF THE INVENTION

Against this background, the object of the invention is to provide a kit comprising various reagents in various vessels that makes it easier to use the reagents in automated laboratory systems. "Making it easier" means both reducing the danger of confusion and/or using as much as possible of the capacity of the vessels filled with reagents.

The object is achieved by a kit with the characteristics of claim 1. Advantageous embodiments of the kit are indicated in the dependent claims.

The kit according to the invention comprises a carrier and vessels arranged on the carrier, wherein different reagents are contained in different vessels, the vessels are arranged with an openable closing device on top of the carrier, the carrier has a footprint on the bottom for being placed on a base, and the carrier possesses bottom positioning means to be positioned on at least one workplace of an automated laboratory system for microtiter plates according to the SBS standard.

In the kit according to the invention, the vessels with the reagents are arranged on a carrier that can be positioned directly on at least one workplace for microtiter plates according to the SBS standard in the work surface of an automated laboratory system. The workplaces of automated laboratory systems are generally designed for the format of microtiter plates according to the SBS standard. The base of the workplaces is adapted to the outer dimensions of the rectangular footprint of microtiter plates according to ANSI/SBS 1-2004: Microplates—Footprint Dimensions. The dimensions are 127.76 mm×85.48 mm, and the tolerances are also standardized. The bases of these workplaces are delimited by stops or other positioning means of the workplaces that ensure that the microtiter plates are precisely positioned. With the epMotion® type automated laboratory systems by Eppendorf AG, the corners of the workplaces are delimited at a right angle by four positioning elements in the form of pins projecting from the work surface. Four positioning elements are firmly connected to the work surface, and one positioning element is movably mounted in the direction of the diagonally opposing corner and is pretensioned by a spring toward the opposing corner. At the opposite corner, there are two positioning elements firmly connected to the work surface. Only one positioning element in each case is at the other corners. The positioning elements contact the corners of a microtiter plate placed on the workplace. The movable positioning element makes it easier to put down the microtiter plate and remove the microtiter plate from the work surface. The movable positioning element presses the microtiter plate against the fixed positioning elements to precisely position the plate on the work surface.

The kit carrier with the vessels arranged thereupon can be positioned directly on at least one workplace. Precise positioning is easy since its positioning means have been adapted to the SBS standard for microtiter plates. The user merely has to open the cover of the vessels and arrange the carrier with the open vessels on a workplace using the positioning means. The controls of the automated laboratory system are aware of the designated workplace for positioning the carrier with the reagents to perform a specific method. In addition, the controls of the automated laboratory system are aware of the provided arrangement of the vessels with the different reagents on the carrier. The automated laboratory system can therefore dip its pipette or another dosing device from the top into the open vessels while performing the method on the basis of the known arrangement of vessels, and remove the corresponding amount of required reagents directly from the vessels and add them to other vessels, or respectively remove them therefrom or process them in another manner. After the reagents of a kit have only been partially consumed, the carrier with the vessels can be removed from the work surface and stored in a refrigerator after the vessels have been closed. Once the kit is used up, the carrier can be discarded together with the vessels and covers in the laboratory waste. The carrier and vessels are preferably designed as economical single-use articles (disposables).

The kit according to the invention overcomes the problem of searching for individual vessels with special reagents and precisely positioning the different vessels. The user merely has to open the vessels and position them with the carrier on the workplace. The risk of confusion is extremely low since the vessels can remain at their assigned places on the carrier.

According to one preferred embodiment, the positioning means of the carrier are designed to position the carrier on a single workplace. The positioning means of the carrier interact with the other positioning means of just one workplace. This embodiment of the carrier positioning means is preferable when the base of the carrier corresponds to the base of the workplace or possibly slightly exceeds it so that the carrier only occupies a single workplace and possibly the space between this workplace and neighboring workplaces. The positioning means of the carrier can also be designed to only interact with the other positioning means of a single workplace when the base of the carrier is large enough to occupy a plurality of workplaces on a work surface of an automated laboratory system. If the dimensions of the carrier are large enough to occupy a plurality of workplaces, the positioning means of the carrier according to another embodiment can be designed to position the carrier with reference to a plurality of workplaces. In this case, the positioning means of the carrier interact with other positioning means of a plurality of workplaces.

According to one embodiment, the positioning means of the carrier are the outer edges of a base of a carrier with dimensions that correspond to the dimensions of at least one workplace of an automated laboratory system for a microtiter plate according to the SBS standard. If the positioning means only interact with the other positioning means of a single workplace, the carrier has bottom outside dimensions that correspond to the outside dimensions of a microtiter plate. This correspondence of the outer dimensions can be limited to the areas of the carrier that interact with the other positioning means of the workplaces. If the other positioning means are pins arranged at the corners of the workplaces, the correspondence of the dimensions can be restricted to the corners of the carrier. However, it is preferable for all the outside dimensions of the bottom edge of the carrier to correspond to the outside dimensions of a microtiter plate according to the SBS standard.

If the positioning means of the carrier interact with other positioning means of a matrix-like arrangement of four workplaces, the positioning means can be designed at four corners of the carrier assigned to the four pins which define the corners of the arrangement consisting of four workplaces. Between the four corners, the carrier can have bottom recesses so that it does not collide with the pins on the outer sides of the arrangement consisting of four workplaces which are arranged between the corners of this arrangement.

According to another embodiment, the positioning means are at least partially designed at a projection extending from the bottom side of the carrier. For example, the outer edge of the bottom of the carrier has a peripheral base or a plurality of feet that forms or that form a footprint or part of the footprint of the carrier. Within the peripheral base or respectively feet, a frame-like projection for example extends downward with outer edges that form the positioning means of the carrier for positioning against the other positioning means of at least one workplace. This embodiment can, for example, be selected for a carrier with a base that is greater than the base of a single workplace. According to another embodiment, the positioning means of the carrier are partly formed by the outer edges of a base of the carrier, and partly by at least one projection extending from the bottom of a carrier within the outer edges. In particular, it is possible that the positioning means are formed by two neighboring outer edges of the base of the carrier, and by a projection extending from the bottom of the carrier within the outer edges. With the outer edges serving as positioning means this carrier can be placed on other positioning means of the workplace so that the positioning means formed by the projection on the bottom are aligned with the corresponding positioning means of the workplace. This makes it easier to position the carrier on a workplace.

According to one preferred embodiment, the vessels are held by retaining means of the carrier. The retaining means are preferably designed so that they hold the vessels with the openable closing device at the top and at specific positions on the carrier so that they do not fall over, especially when being transported. The retaining means can be designed to hold all or some of the vessels aligned vertically when the carriers are placed on a base. The retaining means can also be designed to hold all or some of the vessels aligned at a vertical angle when the carrier is placed on a horizontal base. The last-cited embodiment is the subject of independent claim 3. The retaining means can be designed differently. The retaining means are preferably seats for the carrier in which the vessels can be inserted. According to another embodiment, the retaining means are supporting means that support the vessels. For example, the carrier comprises a plate-shaped storage element and supporting means in the form of a perforated plate that are held at a distance from the main body by means of spacers. The vessels are inserted into holes of the perforated plate, and their vessel bottom rests on the perforated plate.

Furthermore, the object is achieved by a kit with the characteristics of claim 3. Advantageous embodiments of the kit are indicated in the dependent claims.

The kit according to the invention comprises a carrier and vessels arranged on a carrier, wherein different reagents are contained in different vessels, the vessels are arranged with an openable closing device on top of the carrier, the carrier has a footprint on the bottom for being placed on a base, and the vessels are held by retaining means of the carrier, wherein the retaining means hold at least one vessel when the footprint of the carrier is arranged on a horizontal base aligned inclined towards the vertical.

Fluids can be removed from vessels by means of pipettes and other dosing devices only up to a specific fluid level so that residual amounts always remain in the vessels. Conventionally, the vessels are held by the retaining devices in a vertical alignment on the work surface of an automated laboratory system. Consequently, the fluid is evenly distributed over the bottom of the vessel or around a central, elevated bulge in the vessel bottom. Consequently, the residual quantity remaining in the vessels is comparatively large. With the kit according to the invention, at least one vessel is held by the retaining means of the carrier that hold the vessel inclined towards the vertical when the carrier is arranged on the horizontal work surface of an automated laboratory system. Given the inclination towards the vertical, the residual amount of fluid collects at the lowest point of the inclined vessel bottom and can be largely removed by means of a pipette or another dosing device that dips from above into the open vessel. The carrier preferably has many or exclusively retaining means that, when the carrier is arranged on a horizontal base, hold the vessels at an angle to the vertical so that almost all of the reagent can be used in as many vessels as possible. It can however also be advantageous for the carrier to have one or a few of such retaining means that can hold vessels with particularly expensive reagents. The vessels can be vertically aligned by the other retaining means when the carrier is arranged on a horizontal footprint. This makes better use of the space in the carrier.

The kit of claim 3 can advantageously have the features of the kit from one of claims 1 and 2.

According to one embodiment, the retaining means comprise at least one seat for the carrier in which a vessel is arranged, wherein the vessel abuts at least one guide surface in at least one seat that is aligned so that the vessel is inclined towards the vertical when the footprint of the carrier is arranged on a horizontal base. The vessel is kept in the seat so that it does not tip over. The guide surface is a bottom and/or a side wall of the seat. The guide surface is preferably formed by a bottom and side wall of the seat. The guide surface can be a continuous, flat surface. The guide surface can also be formed from a plurality of partial surfaces with gaps in between.

According to a preferred embodiment, the guide surface is a bottom of the seat that is inclined at an angle to the footprint, and the vessel rests on it. When the carrier rests on the horizontal base, the bottom is inclined towards the horizontal so that the vessel resting on it is inclined towards the vertical. A side wall of the seat preferably forms another guide surface that supports the side of the vessel.

According to another embodiment, the vessel lies in the seat with the inclined bottom at a top opening on one side at a side wall section of the seat and not on the opposing side so that a viewer can observe an identification on the side of the vessel through the top opening in the seat. Between the inclined vessel and the carrier, there remains a gap in the region of the top opening through which the viewer can see the side of the vessel. This allows the viewer to read the identification on the side of the vessel to check whether the vessel is assuming the position on the carrier that is presumed by the controls of the automated laboratory system. Despite the gap between the vessel and the seat, the vessel is held in a stable position in the seat due to the inclination of the bottom.

According to another embodiment, the cross-section of the seat with the inclined bottom expands upward to the opening in the seat. This makes it easier to read an identification. In addition, it is advantageous in terms of production for the cross-section of the seat to expand upward since it makes it easier to injection-mold the carrier using a two-part mold.

According to another embodiment, the carrier as a top wall and containers that extend downward from the top wall, wherein the openings in the seats are formed in the top wall, and the seats are formed in the containers. This embodiment saves material and is easy to manufacture.

According to another embodiment, the footprint is formed on the bottom side of the bottoms of the seats. This also saves material and reduces the amount of effort involved in production. In another embodiment, the footprint is formed by the bottom edge of a frame that extends downward from the edge of the top wall. In another embodiment, the footprint is formed by the bottom ends of feet that extend downward from the top wall.

According to another embodiment, the containers extend downward from the top wall to different lengths, and the containers projecting furthest downward form the footprint with the bottom side of their bottoms. Containers with small seats for small vessels can extend downward less than containers with seats for large vessels. This also saves material.

According to another embodiment, the seat with the inclined bottom has two inclined bottom sections at a distance from each other, and a bottom section therebetween that with the bottom side forms a section of the footprint. This allows the footprint to be formed on a section of an inclined bottom. The inclined bottom surfaces at a distance from each other ensure that the vessel does not tip over in the seat even if the seat expands upward.

According to one embodiment, the carrier has a main body that carries the vessels and an adapter that holds the main body with the footprint on the bottom side, or the carrier is a main body that carries the vessels with the footprint on the bottom side. In the first variant, the adapter with the footprint can be positioned on the work surface of the automated laboratory system. The adopter holds is the main body that bears the vessels. The adapter can serve to position the vessels at a level that can be reached by a pipette or another dosing device of the automated laboratory system. In this embodiment, the main body preferably has its own footprint on the bottom side that can be used to place the main body on a base without the adapter. The footprint of the main body is preferably aligned parallel to the footprint of the adapter so that at least one vessel can also be aligned inclined towards the vertical, even when the footprint of the main body is placed on a base.

In the second variant, the carrier is a main body that bears the vessels and has the footprint. The main body can be positioned directly on the work surface. There is no adapter.

According to one embodiment of the kit, the carrier comprises a main body having the retaining means and an adapter holding the main body with the footprint on the bottom side, or the carrier is a main body that has the retaining means and the footprint on the bottom side. In the first variant, the main body preferably has at least one retaining means that holds a vessel inclined towards the vertical when the footprint of the main body is arranged on a horizontal base. It is however also possible for the main body to have exclusively retaining means that keep the vessels aligned vertically when the footprint of the main body is arranged on a horizontal base. The inclination of the vessels relative to the footprint of the adapter can be realized in this embodiment by the adapter holding the main body at an inclined alignment to the footprint of the adapter.

In one embodiment, the adapter has a frame with the footprint on the bottom side of a bottom part and a top part protruding laterally above the bottom part to receive the main body, and/or in the main body has a bottom part with the footprint on the bottom side and a top part protruding laterally above the bottom part to receive the vessels. According to another embodiment, the outer edges of the bottom part are the positioning means. These embodiments allow gaps between the workplaces of an automated laboratory system to be used by carriers on which a plurality of or respectively large vessels are arranged. In the first variant, the adapter allows a main body to be used with a base larger than the base of the adapter. In the second variant, the main body accommodates the vessels in a top part, wherein the top part has a cross-section that is greater than the footprint of the main body.

In another embodiment, the adapter has two flat opposing housing walls that extend over the entire height of the bottom part and top part, the adapter has two housing wall sections in each case aligned perpendicular to the opposing side wall in the region of the bottom part at the two edges of the housing walls, and in the region of the top part, the two opposing housing walls are connected to each other at their side edges by additional housing walls while projecting outward above the angled housing wall sections. This adapter makes it possible to use main bodies with a base larger than the base of the bottom part. The structural design of this adapter is particularly simple.

According to another embodiment, the vessels have IDs on a vessel body and/or a vessel cover, and corresponding IDs are arranged on a top wall of the carrier next to openings in the seats formed therein. This makes it possible for the user to check whether the vessels are arranged at the intended positions assumed by the controls of the automated laboratory system. If necessary, the user can correctly position the vessels according to the IDs. The IDs on the vessel covers make it easier to assign the vessel covers to the vessels when they are to be closed and stored intermediately. The IDs on the vessel bodies make it easier to assign the vessels to the seats even when the covers are removed. According to one embodiment, the IDs are color codes, barcodes, numerical codes, or a combination of one or more of the aforementioned types of codes.

According to another embodiment, a top wall of the carrier has at least one additional ID that is scannable with a sensor, and/or at least one surface for writing and/or a label. The additional ID can in particular identify the type of the kit. The automated laboratory system can scan the additional ID using a sensor and check whether the reagents needed to perform the method are arranged on the workplace, or respectively whether they are arranged at the intended position. If the automated laboratory system does not identify the needed reagents, the automated laboratory system can output a warning. If the reagents are not located at the intended position, the automated laboratory system can also output a warning or modify the method so that the reagents are also used according to the method even at the position that they have assumed. The automated laboratory system can identify an incorrect positioning at the correct workplace if the ID is arranged at a specific position or respectively in a specific alignment on the carrier. The automated laboratory system uses the position or alignment of the ID relative to the carrier to determine whether the carrier is correctly positioned on the relevant workplace. According to one embodiment, the additional ID is formed by one or more holes in a top wall of the storage element. According to a preferred embodiment, the top wall has a series of a plurality of holes at a specific location, and a label is arranged on the top wall that covers all, or only some of the holes, or no holes. The label can have additional holes above the holes for this purpose. The code is determined by the number and arrangement of uncovered or respectively covered holes. This embodiment makes it particularly easy to change the code.

The surface for writing and/or the label on the carrier is dimensioned so as to allow writing, a label or another ID which is legible by a user with normal vision without visual aid.

According to another embodiment, the carrier is shaped in a complementary manner on the bottom side and on the top side with and without vessels arranged thereupon such that a plurality of carriers can be stacked upon each other with and without vessels arranged thereupon. This makes it possible to transport and store a plurality of kits according to the invention in a space-saving manner.

The vessel cover is a cover that can be screwed on, clipped on, and laminated and consists of a metal foil or another foil. In addition, the cover can be a through-hole cover. The vessel sets can be equipped with covers of the same kind or a different kind.

According to another embodiment, the carrier is provided with a cover. The cover serves to protect the kit or respectively vessels during storage and transport. The connection between the cover and carrier is preferably configured so that the carrier can be removed and mounted manually or by a gripper of an automated laboratory system.

According to another embodiment, the kit comprises external packaging in which at least one carrier is arranged with vessels arranged thereupon with or without covers. The external packaging is used for storing, transporting and shipping the kit. The user can remove the carrier with the vessels arranged thereupon from the external packaging and place it on an automated laboratory system.

According to another embodiment, the kit comprises a stack of carriers with vessels arranged thereupon, and/or a bag containing reaction vessels in an external packaging. The number of carriers and vessels and/or reaction vessels is calculated to be sufficient to perform a given number of investigations.

According to another embodiment, the main body consists of at least one injection-molded plastic, or at least one plastic and/or another material that is deep-drawn or mechanically produced.

According to another embodiment, the vessels are made of at least one injection-molded plastic, and/or at least one plastic from a blow-molding process, and/or made of glass, and/or deep drawn from at least one plastic and/or another material.

According to another embodiment, the adapter consists of at least one injection-molded plastic, or at least one plastic or another material that is deep-drawn or mechanically produced.

According to another embodiment, the cover consists of at least one injection-molded plastic, or at least one plastic or another material that is deep-drawn or mechanically produced.

According to another embodiment, the external packaging is a folding box made of cardboard and/or corrugated cardboard.

According to another embodiment, the plastic for the carrier and/or cover and/or the vessels consists of polypropylene.

According to another embodiment, the adapter material is aluminum or another metal.

In addition, the invention relates to a carrier according to the claims and the use of a carrier or kit according to the claims.

BRIEF DESCRIPTION OF THE SEVERAL VIEWS OF THE DRAWINGS

The invention is explained in the following in more detail using the attached drawings of an exemplary embodiment. In the drawings:

FIG. 4 shows a vertical section of the main body of a carrier along line IV-IV from FIG. 1;

FIG. 5 shows a vertical section of the main body of a carrier along line V-V from FIG. 1;

FIG. 6 shows a front view of two stacked main bodies of a carrier;

FIG. 23 shows a vertical section of the immersion of a pipette tip in a vertically aligned vessel with an upwardly bulging bottom;

FIG. 24 shows a vertical section of the immersion of a pipette tip in a vertically aligned vessel with a downwardly bulging bottom;

DETAILED DESCRIPTION OF THE INVENTION

Figure 1:
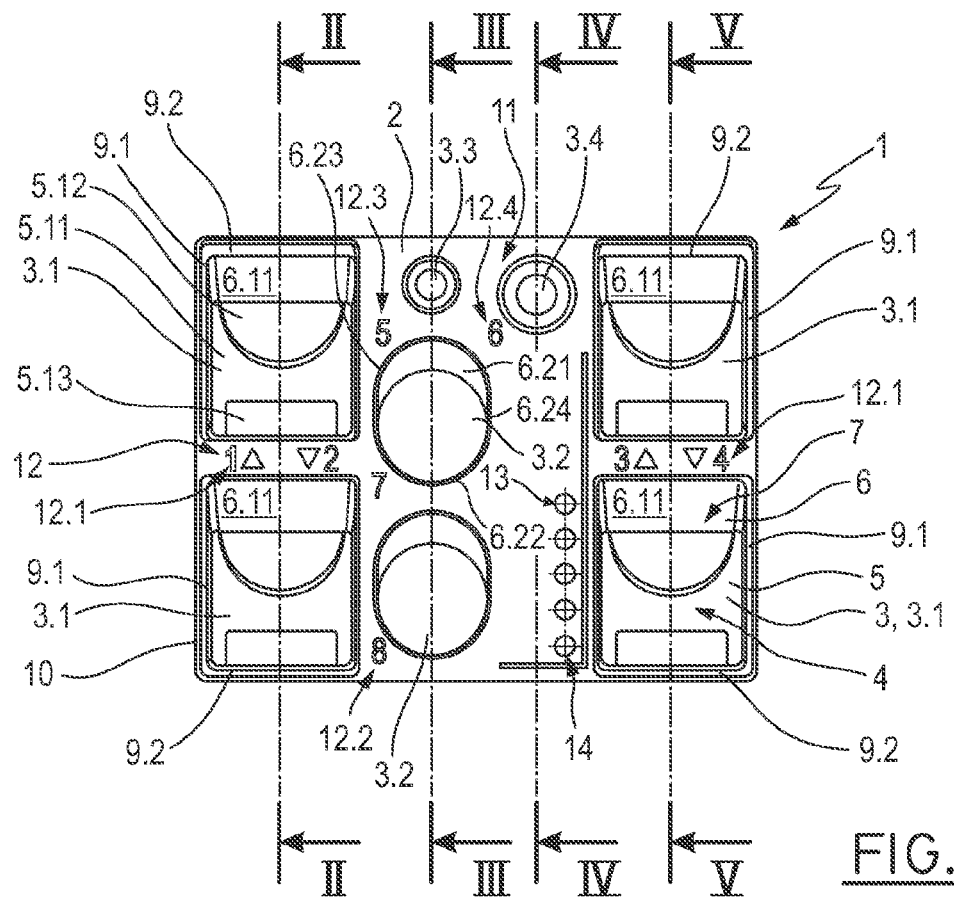
FIG. 1 shows a plan view of a main body of a carrier.

While this invention may be embodied in many different forms, there are described in detail herein a specific preferred embodiment of the invention. This description is an exemplification of the principles of the invention and is not intended to limit the invention to the particular embodiment illustrated.

In the present application, the descriptions "top" and "bottom" and other positional descriptions relate to an arrangement of the carrier with the footprint on a horizontal base.

According to FIGS. 1 to 5, a main body 1 has a rectangular top wall 2 which has containers 3 that project from the bottom side and each have a seat 4 for vessels. The containers 3 each have a bottom 5 and a side wall 6 extending from the bottom to the top wall. In the top wall 2, the containers 3 each have a top opening 7. Each seat 4 is accessible from the outside through the top opening 7.

The main body 1 has four different types of containers 3 and seats 4. A container 3.1 having a seat 4.1, a rectangular bottom 5.1, a side wall 6.1, and a top opening 7.1 is arranged at each of the four corners of the main body. The containers 3.1 extend downward the furthest from the top wall 2. The containers 3.1 each have a rectangular cross section, wherein the cross-section expands from bottom to top. The containers 3.1 each have bottom sections 5.11 of the bottom 5.1 that are aligned parallel to the top wall, and their bottom sides together belong to a footprint 8.1 of the main body 1.

In addition, each container 3.1 has flat bottom sections 5.12, 5.13 inclined at an acute angle to the footprint 8. The inclined bottom sections 5.12, 5.13 are separated from each other by a part of the bottom section 5.11 extending parallel to the top wall 2.

The inclined bottom sections 5.12, 5.13 of the containers 3.1 are inclined in a vertical section parallel towards the short sides of the top wall 2. The inclined bottom sections 5.12, 5.13 of each container 3.1 are arranged in a common plane. The inclined bottom sections 5.12, 5.13 of all the containers 3.1 are aligned parallel to each other.

According to FIG. 1, the bottom section 5.11 of the bottom 5 extending parallel to the top wall 2 is bordered on one side by the inclined bottom section 5.12 which is semicircular in the plan view, and on the other side by the inclined bottom section 5.13 that is rectangular in the plan view. According to FIG. 2, the semicircular bottom section 5.12 is arranged closer to the footprint 8.1 than the rectangular bottom section 5.13.

Each container 3.1 has a side wall section 6.11 that is inclined at an acute angle towards the top wall 2 and is aligned at a right angle to the inclined bottom sections 5.12, 5.13. The side wall sections 6.11 of all the containers 3.1 inclined at an acute angle towards the top wall 2 are parallel to each other.

The remaining sidewall sections 6.12, 6.13, 6.14 of each container 3.1 are arranged approximately perpendicular to the top wall of the main body. The two sidewall sections 6.13, 6.14 of the containers 3.1 are each slightly inclined relative to each other so that their spacing decreases slightly as the distance from the top wall 2 increases. This is shown in FIG. 6.

Figure 2:
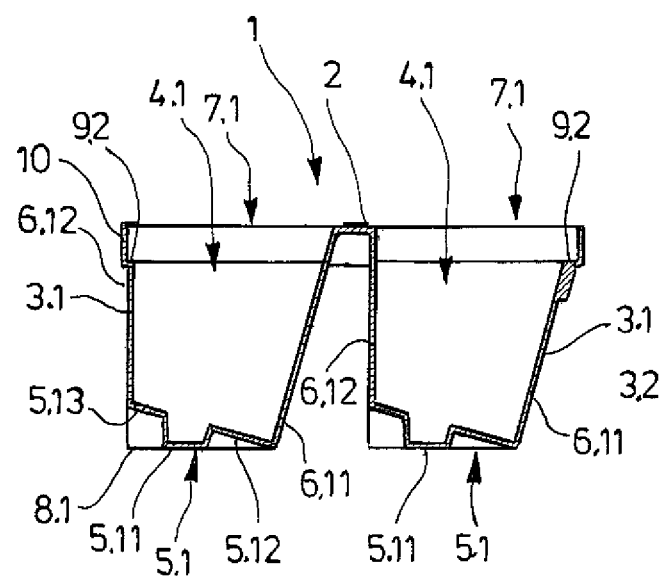
FIG. 2 shows a vertical section of the main body of a carrier along line II-II from FIG. 1.

Next to the top opening 7.1, the containers 3.1 each have a small step 9.1, 9.2 which is shown in FIGS. 1, 2 and 5 and neighbors the short side and long side of the top wall.

The edges of the top wall 2 are delimited and stabilized by an edging 10 extending slightly downward. In the region of the containers 3.1, the edging 10 is formed above the steps 9.1, 9.2 by the top edge regions of the side wall sections 6.11 to 6.14 of the containers 3.1 aligned vertically upward.

In the gap 11 between the two pairs of containers 3.1, two containers 3.2 are arranged next to each other with a seat 4.2 and a top opening 7.2. These containers 3.2 extend downward from the top wall 2 less than the containers 3.1. They are arranged next to each other parallel to the narrow side of the top wall 2. They have a circular, flat bottom 5.2 that as a whole is inclined at an angle towards the footprint 8.1.

The inclined bottoms 5.2 of all the containers 3.2 are aligned parallel to each other. The bottoms 5.2 are inclined in a vertical section parallel to the short sides of the top wall 2.

Figure 3:
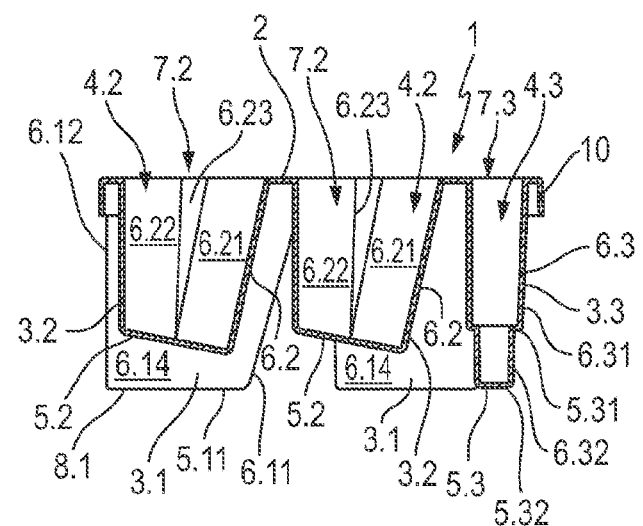
FIG. 3 shows a vertical section of the main body of a carrier along line III-III from FIG. 1.

The containers 3.2 each have a side wall 6.2 with a semi-cylindrical side wall section 6.21 that, according to FIGS. 3 and 4, is aligned perpendicular to the bottom 5.2 and 4 at an acute angle to the top wall 2. In addition, the side wall 6.2 of each container 3.2 has another semi-cylindrical side wall section 6.22 that is aligned perpendicular to the top wall 2 and, according to FIG. 3 and FIG. 4, meets the bottom 5.2 at an obtuse angle. The axes of the semi-cylindrical sidewall sections 6.21, 6.22 are arranged in a vertical section running parallel to the short sides of the top wall 2.

The two semi-cylindrical side wall sections 6.21, 6.22 of the containers 3.2 are connected to each other by flat sidewall sections 6.23, 6.24 whose width increases from bottom to top, and that are aligned perpendicular to the top wall 2 and parallel to the narrow sides of the top wall 2. According to FIG. 3, these side wall sections 6.23, 6.24 are basically triangular. Accordingly, the cross-section of the containers 3.2 increases from bottom to top.

In addition, the containers 3.3, 3.4 with seats 4.3, 4.4, bottom 5.3, 5.4, side walls 6.3, 6.4 and top openings 7.3, 7.4 are arranged in the gap 11 between the two pairs of containers 3.1 next to a long side of the top wall 2. The containers 3.3, 3.4 are circular-cylindrical, wherein the cylinder axis is aligned perpendicular to the top wall 2.

At the bottom end of a top side wall section 6.31, 6.41, the containers 3.3, 3.4 each have a top bottom section 5.31, 5.41 that is aligned parallel to the top wall 2. A bottom hollow cylindrical side wall section 6.32, 6.42 ends in the top bottom section 5.31, 5.41 and is sealed at the bottom by a lower bottom section 5.32, 5.42. The bottom sides of the lower bottom sections 5.32, 5.42 are each part of the footprint 8.1 of the main body 1.

The container 3.3 has a smaller cross-section than the container 3.4.

An ID 12 in the form of a number is adjacent to each container 3.1 to 3.4. The IDs 12.1 of the containers 3.1 are each arranged between two neighboring containers 3.1, wherein an arrow arranged next to the number indicates for which container 3.1 the number applies in each case.

In addition, a series of holes 14 are arranged in the top wall for another ID 13. The series of holes 14 is aligned parallel to the short side of the top wall 2. The main body 1 is manufactured as a single part by injection-molding a plastic. The plastic is for example, polypropylene.

According to FIGS. 2 to 5, the main body 1 can be placed on a horizontal base, wherein the footprint 8.1 rests on the horizontal base on the bottom side of the bottom sections 5.1, 5.32, 5.42 of the vessels 3.1, 3.3, 3.4.

Figure 7:
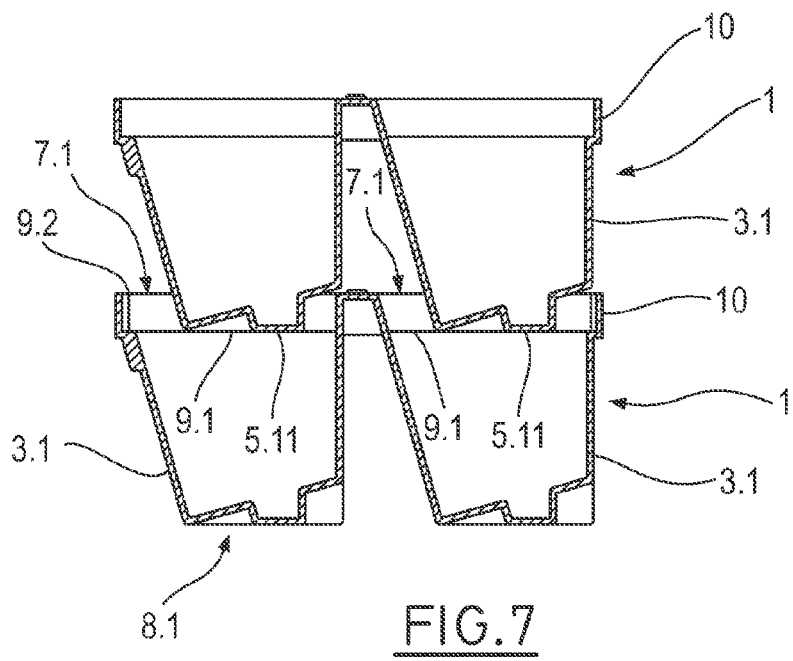
FIG. 7 shows the stacked main bodies of a carrier in a vertical section VII-VII from FIG. 6.
Figure 8:
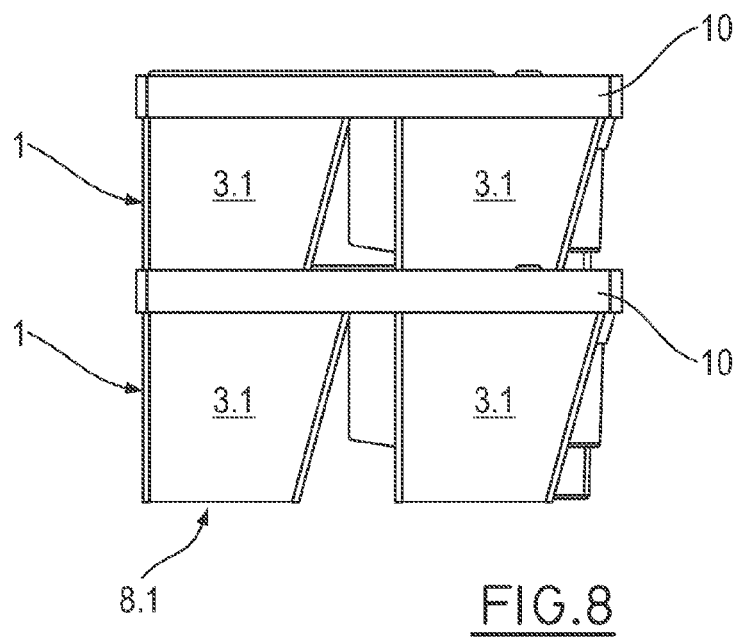
FIG. 8 shows a side view of the stacked main bodies of a carrier.
Figure 9:
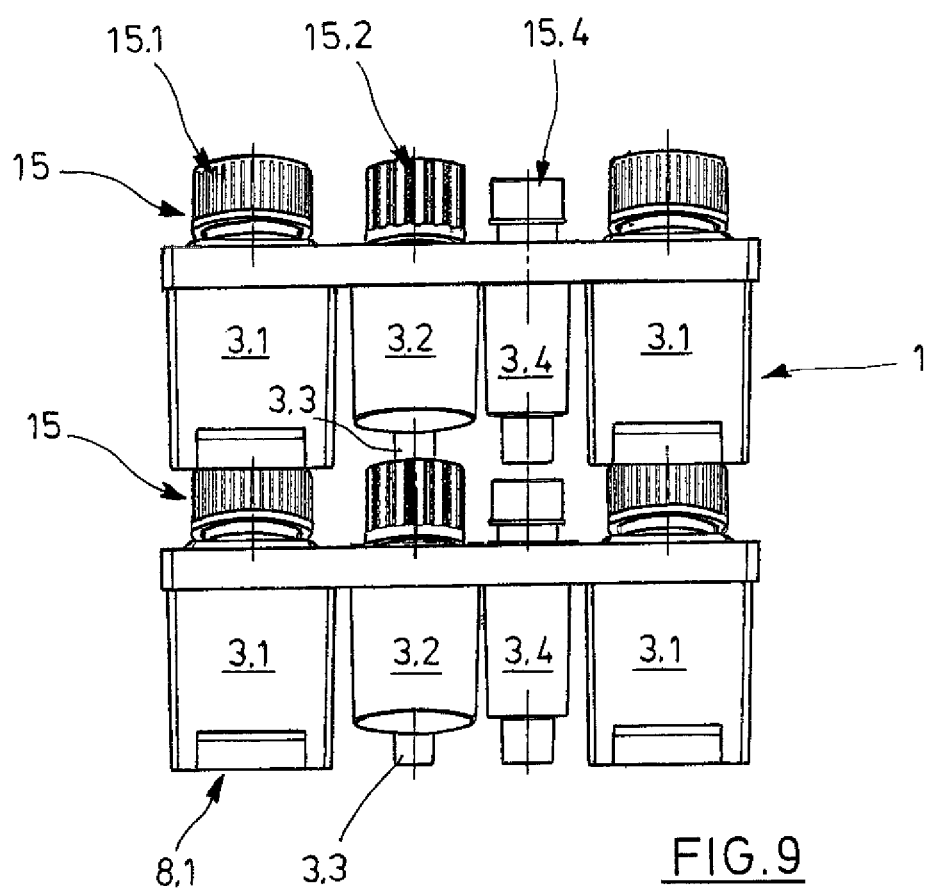
FIG. 9 shows a front view of two stacked main bodies of a carrier equipped with vessels.

According to FIGS. 6 to 8, two or more identical main bodies 1 can be stacked on each other. The bottom sections 5.11 of the containers 3.1 of the top main body 1 rest on the steps 9.1, 9.2 below the top openings 7.1 of the containers 3.1 of the bottom main body 1. Horizontal shifting of the main bodies 1 relative to each other is prevented since the containers 3.1 of the top main body 1 engage in the top openings 7.1 of the containers 3.1 of the bottom main body 1.

According to FIGS. 9 to 12, vessels 15 are inserted in the seats 4 of the main body 1. These are vessels 15 or vials that have a vessel body 16 and a screwable vessel cover 17. There are four different types of vessels 15.1 to 15.4, wherein at least some of the vessels 15 contain different reagents.

Instead of the vessels 15.3, 15.4 with the screwable vessel cover 17.3, 17.4, reaction vessels can be inserted in the seats 4.3, 4.4 that have a vessel cover in the form of a pressed-in plug, wherein the vessel cover can be connected to the vessel body by means of an integrated cover holder. The integrated cover holder is, for example, a molded-on flexible tab that connects the vessel cover and vessel body to each other as a single part. To hold the vessel cover in the open position, the main body 1 according to one embodiment is provided with a holder as described in WO 2008/003338 A1 with reference to FIG. 9, position 44. The related embodiments in WO 2008/003338 A1 are included in the present application by means of reference. With a main body 1 having such a design, the reaction vessel is inserted from above into the main body 1. To be transported, the vessel is closed with the cover molded onto the vessel. If the user wishes to open the vessel, he can lift the vessel slightly, open the cover, and place the vessel back in the opening while threading the cover into the molded-on cover holder. The cover then extends vertically upward and therefore does not interfere with the removal of fluid from the vessel in the automated system.

Vessels 15.1 with a vessel body 16.1 having a rectangular cross section are inserted into the container 3.1. The containers 3.2 to 3.4 accommodate vessels 15.2 to 15.4 with a vessel body 16.1 to 16.4 having a circular cross-section.

The bottom sections 5.12, 5.13 and the bottom 5.2 as well as the side wall sections 6.11, 6.21 are guide surfaces that align the vessels 15.1, 15.2. The vessels 15.1, 15.2 each rest on the bottom sections 5.12, 5.13 or respectively the bottom 5.2 and lie against a side wall section 6.11 or respectively 6.21 of the seats 4.1, 4.2. This causes the vessels 15.1, 15.2 in the containers 3.1 and 3.2 to be arranged inclined at an angle towards the vertical when the footprint 8.1 of the main body 1 rests on a horizontal base as shown in FIGS. 9 to 12.

Since the cross-section of the seats 4.1, 4.2 expands from bottom to top, a viewer is able to look from above onto the side of the vessel body 16.1, 16.2. This is illustrated in particular in FIGS. 10 and 11.

The vessels 15.3, 15.4 are kept vertically aligned in the seats 4.3, 4.4 of the containers 3.3, 4.4 by the bottom sections 5.31, 5.41 and the side wall sections 6.31, 6.41.

Figure 10:
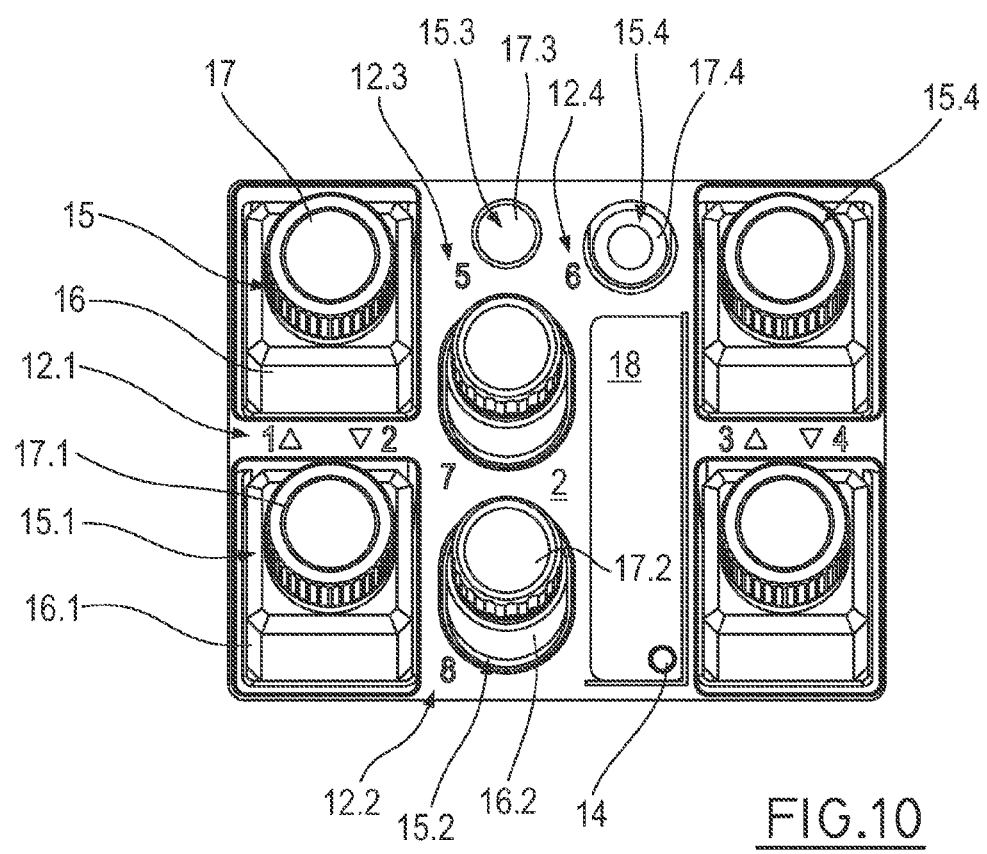
FIG. 10 shows a plan view of a main body of a carrier equipped with vessels.
Figure 11:
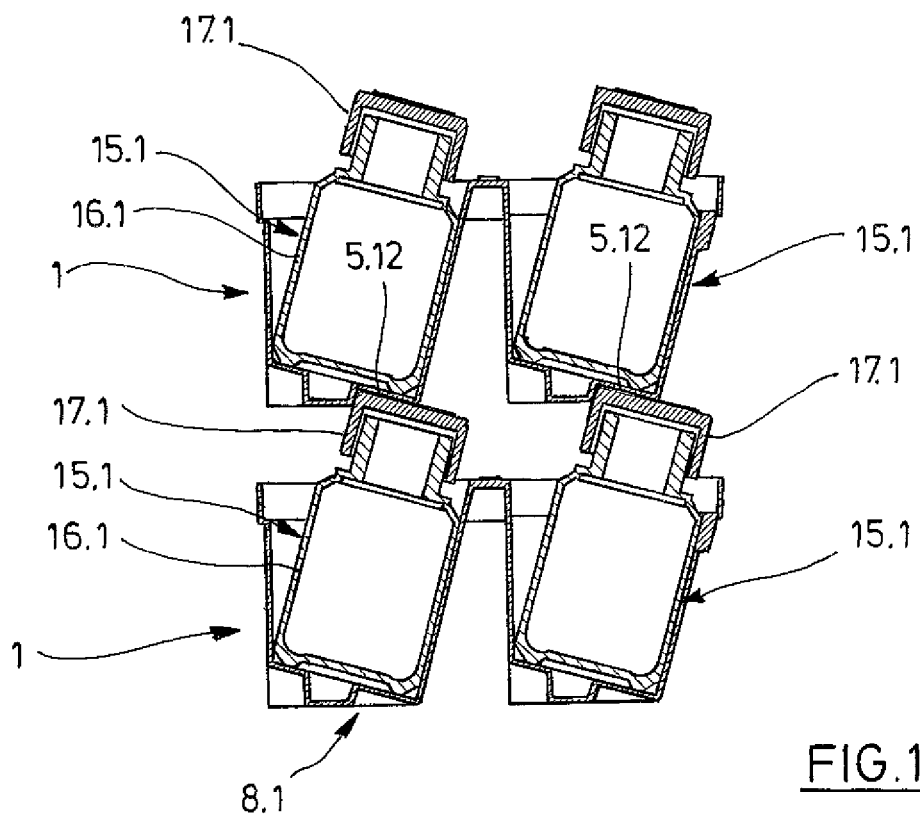
FIG. 11 shows the stacked main bodies of a carrier equipped with vessels in a section along line XI-XI from FIG. 9.
Figure 12:
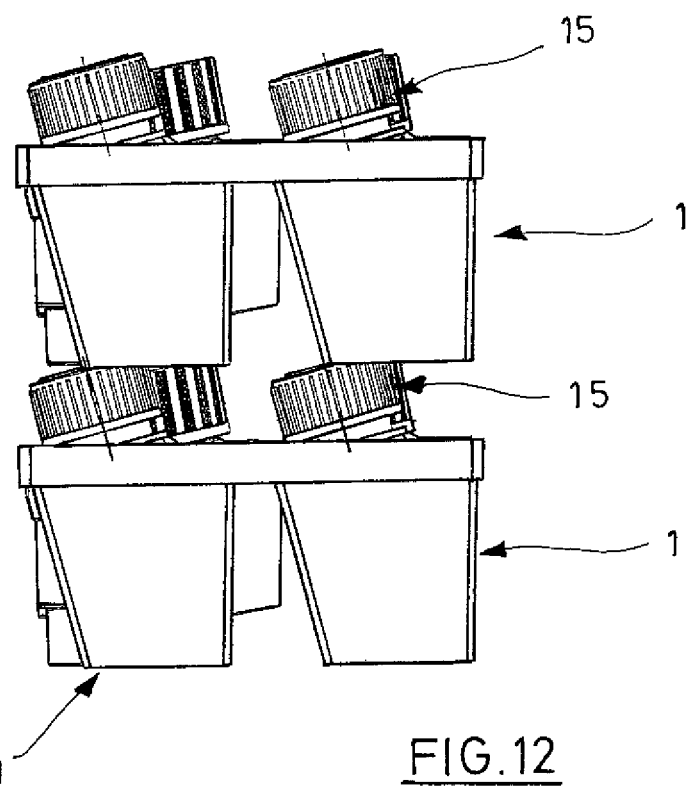
FIG. 12 shows a side view of the stacked main bodies of a carrier equipped with vessels.

According to FIG. 10, the gap 11 between the two pairs of containers 3.1 bears a label 18 that only leaves one of the holes 14 of the main body 1 free and covers the other holes 14. This provides a code for the arrangement consisting of the main body 1 and the vessels 15.

On the sides of the vessel body 16.1 to 16.4 and at the top on the vessel cover 17.1 to 17.4, the vessels 15 bear an ID that corresponds to the ID 12.1 to 12.4 on the top wall 2 next to the container 3.1 to 3.4 that accommodates the respective vessel 15. The IDs of the vessels are not shown in figures.

A plurality of main bodies 1 equipped with vessels 15 are stacked on each other. The bottom side of the semicircular, inclined bottom sections 5.12 of the top main body 1 rests on the vessel covers 17.1 of the vessels 15.1 in the main body 1 arranged below.

Since the vessel covers 17.1 lie against the inclined bottom sections 5.12 and the sides of neighboring bottom sections 5.11 of the top main body 1, the main bodies 1 are secured relative to each other from being shifted in a horizontal direction.

The user is provided with the main bodies 1 equipped with vessels 15 in a stacked or unstacked arrangement.

Figure 13:
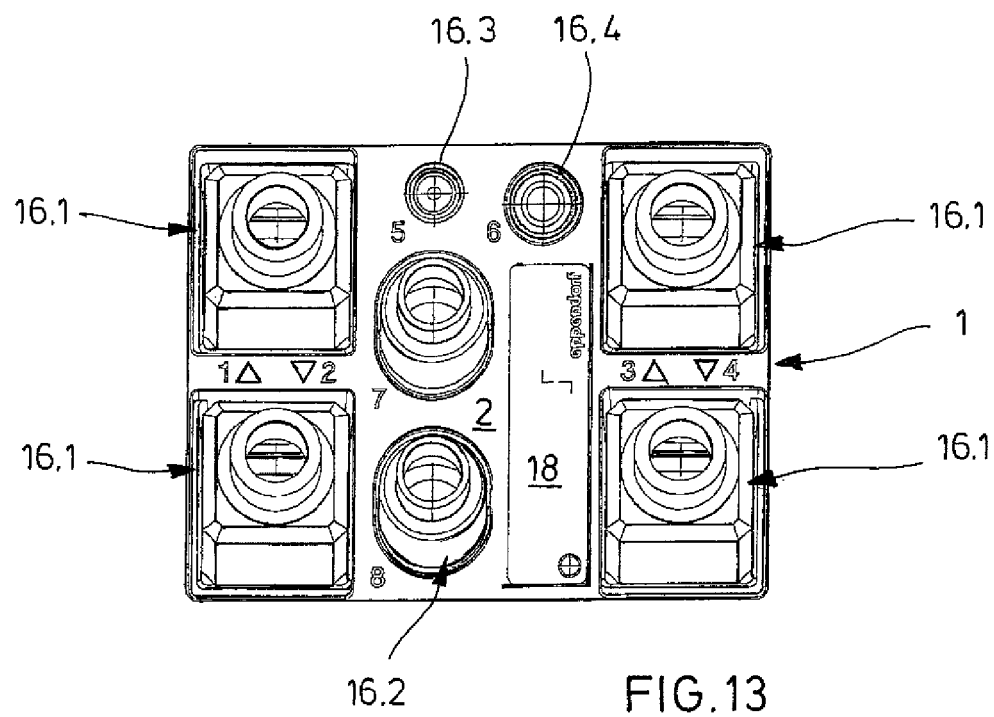
FIG. 13 shows a plan view of a main body of a carrier equipped with vessels without vessel covers.
Figure 14:
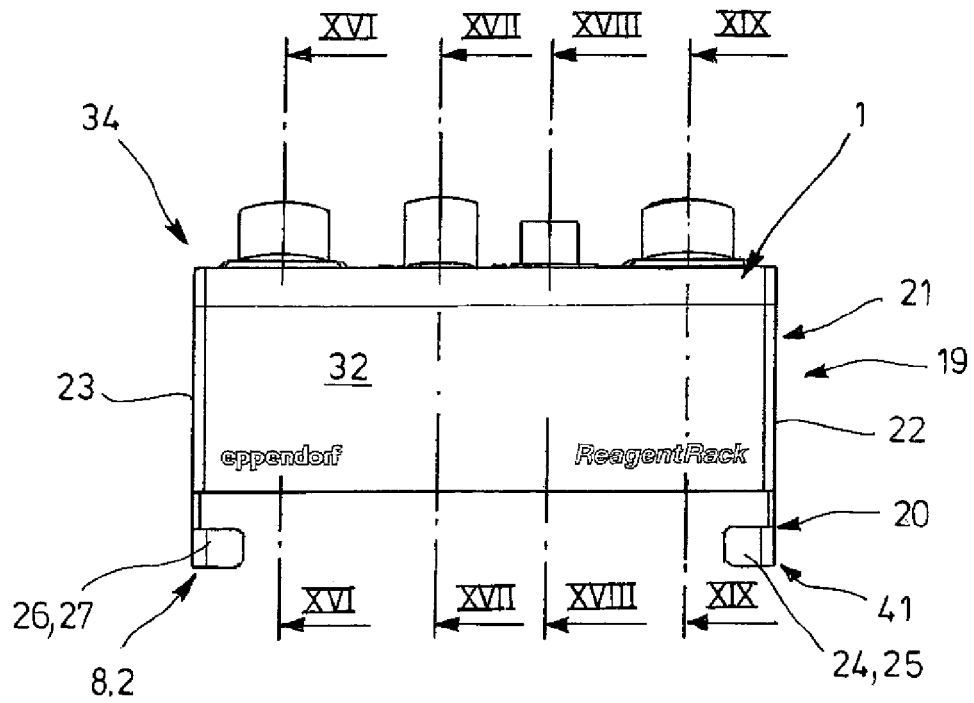
FIG. 14 shows a front view of a carrier comprising a main body equipped with vessels and an adapter.
Figure 15:
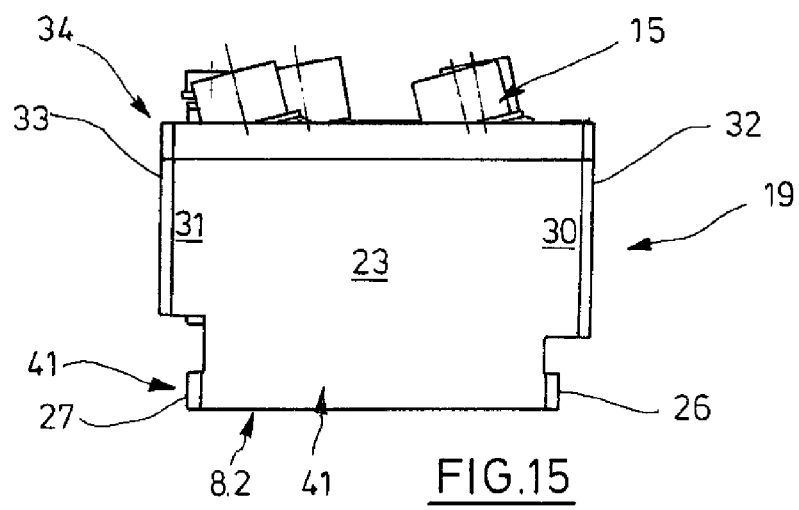
FIG. 15 shows a side view of the carrier equipped with vessels.
Figures 16, 17:
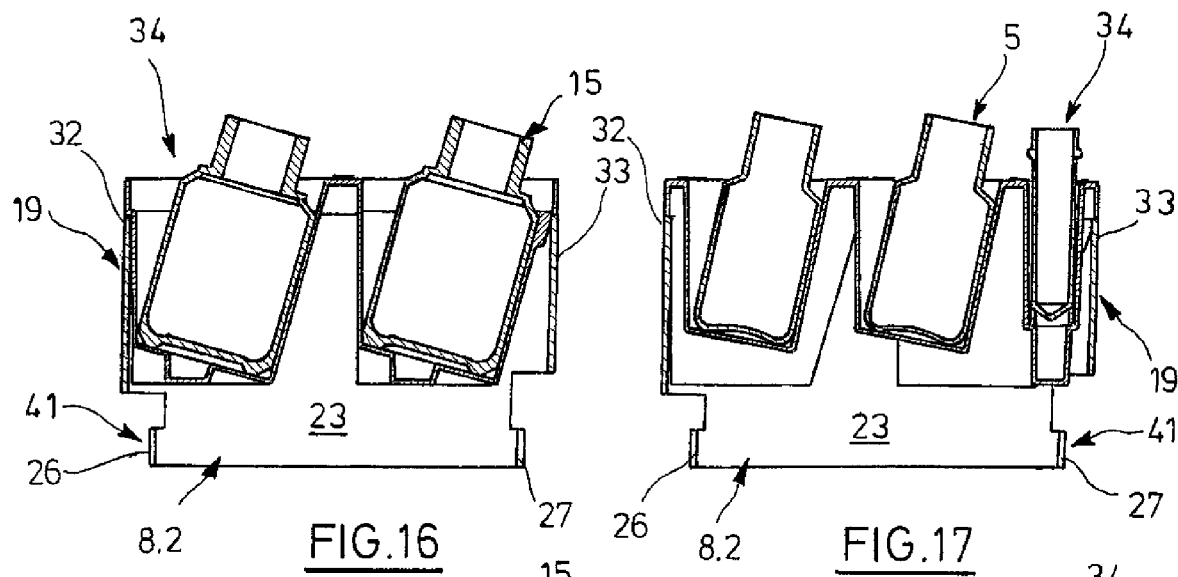
FIG. 16 shows the carrier equipped with vessels without vessel covers in a section along line XVI-XVI from FIG. 14.
FIG. 17 shows the carrier equipped with vessels without vessel covers in a section along line XVII-XVII from FIG. 14.
Figures 18, 19:
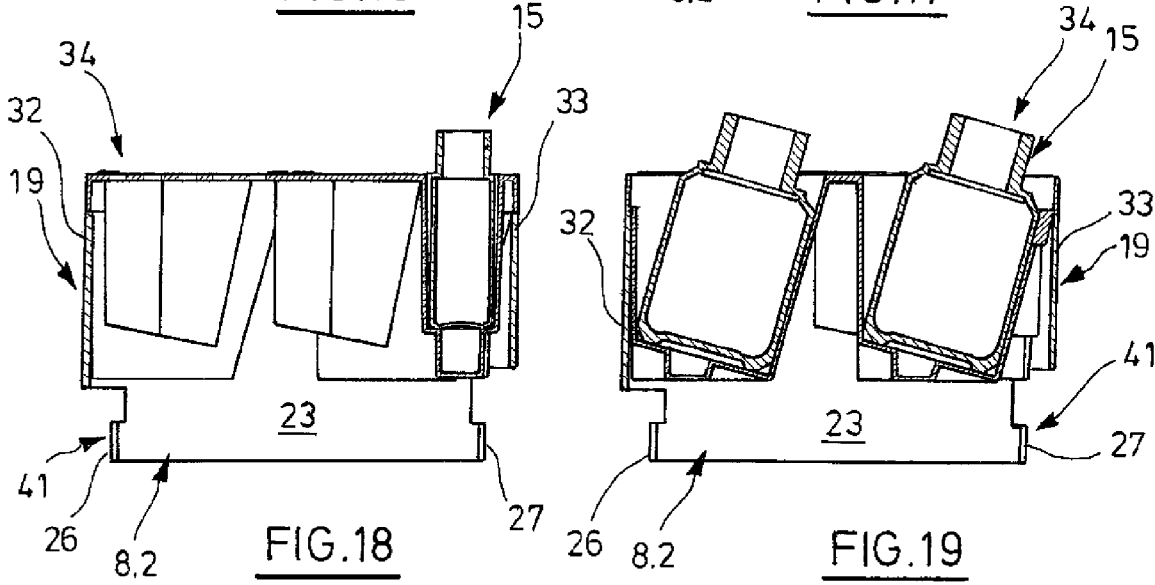
FIG. 18 shows the carrier equipped with vessels without vessel covers in a section along line XVIII-XVIII from FIG. 14.
FIG. 19 shows the carrier equipped with vessels without vessel covers in a section along line XIX-XIX from FIG. 14.

According to FIG. 13, the user can remove the vessel covers 17.1 to 17.4 from the vessels 15.1 to 15.4 before removing the reagents.

If the user is not using an automated laboratory system, he can place the footprint 8.1 of the storage element on a flat base and remove reagent from the vessels using a pipette. If the user is working with an automated laboratory system, he can insert the main body 1 with the open vessels 15.1 to 15.4 into an automated laboratory system. If the outer edges of the footprint 8.1 are suitably dimensioned, the user can position the storage element directly on a workplace for microtiter plates of the automated laboratory system. In the exemplary embodiment, the outer dimensions of the footprint are greater than the workplace of an automated laboratory system.

Consequently, the adapter 19 according to FIGS. 14 to 19 is used to position the main body 1 in the automated laboratory system. The adapter 19 has a basically box-shaped housing. The adapter 19 has a bottom part 20 with a footprint 8.2 that can be placed on a workplace of the automated laboratory system, as well as a top part 21 that accommodates the main body 1. The footprint 8.2 of the adapter 19 is parallel to the footprint 8.1 of the employed main body 1.

The adapter 19 has two opposing housing walls 22, 23 that extend over the entire height of the bottom part 20 and the top part 21. In the region of the bottom part, these housing walls 22, 23 each have two tab-shaped housing wall sections 24, 25, 26, 27 aligned perpendicularly to the opposing housing wall 23, 22. In the region of the top part 21, the two opposing housing walls 22, 23 project outward in edge areas 28, 29, 30, 31 above the angled housing wall sections 24 to 27 and are connected to each other at their side edges by means of additional housing walls 32, 33. The two housing walls 22, 23 form the two short sides of the adapter 19. The two other housing walls 32, 33 form the long sides of the adapter 19.

Figure 20:
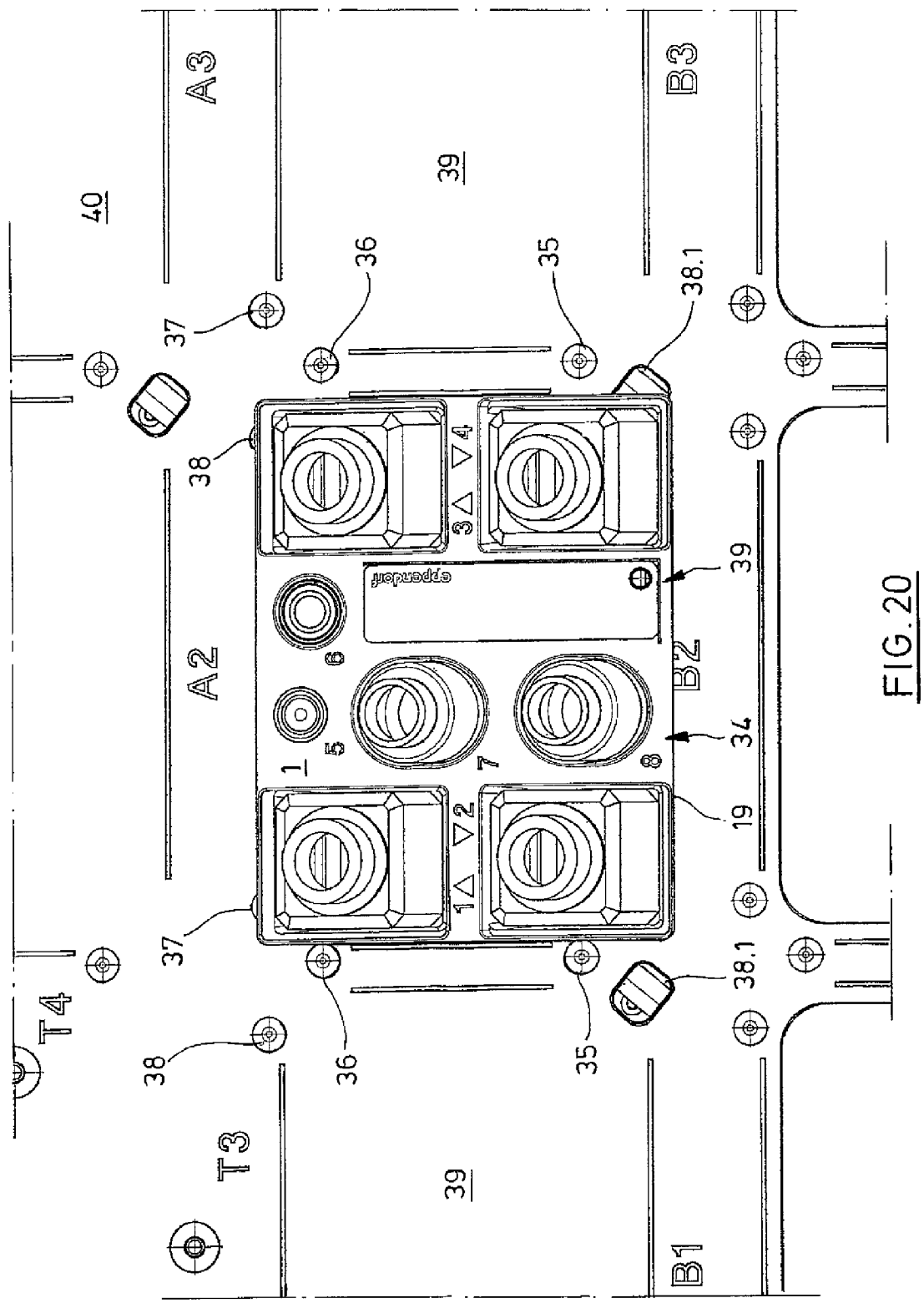
FIG. 20 shows the carrier equipped with vessels without vessel covers on the workplace of an automated laboratory system.

According to FIG. 20, the carrier 34 formed by the main body 1 and adapter 19 with the open vessels 15 arranged therein between fixed pins 35 to 38 and a movable pin 38.1 is positioned on a workplace 39 of an automated laboratory system 40. The outside bottom edges of the housing walls 22, 23 and the housing wall sections 24 to 27 are positioning means 41 that align against the pins 35 to 38.1 which are additional positioning means 42.

Figure 21:
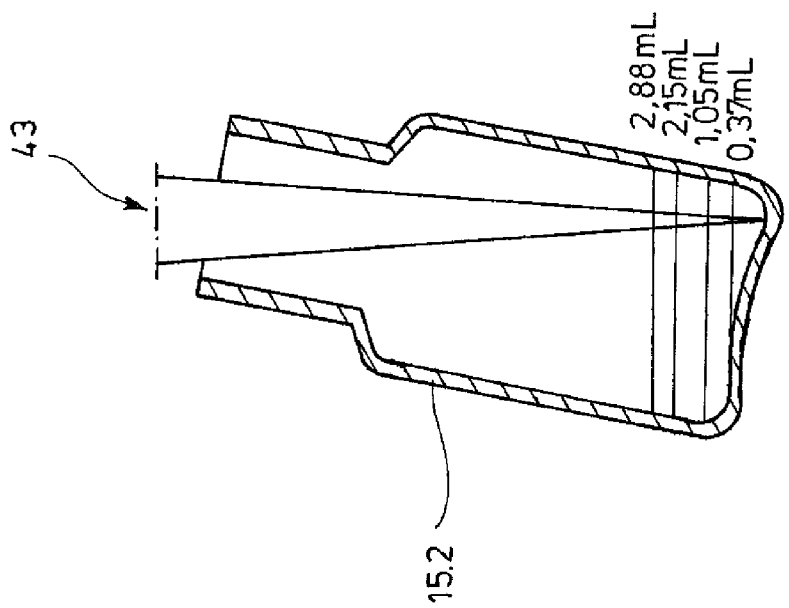
FIG. 21 shows a vertical section of the immersion of the pipette tip in an inclined vessel.

FIG. 21 shows the vessel 15.2 when fluid is being removed by means of a pipette tip 43 of a pipette. Almost all of the reagent can be removed due to the inclined arrangement of the vessel 15.2 in the seat 4.2 of the carrier 34. Only a slight residual amount cannot be drawn from the lowest point in the vessel 15.2.

Figure 22:
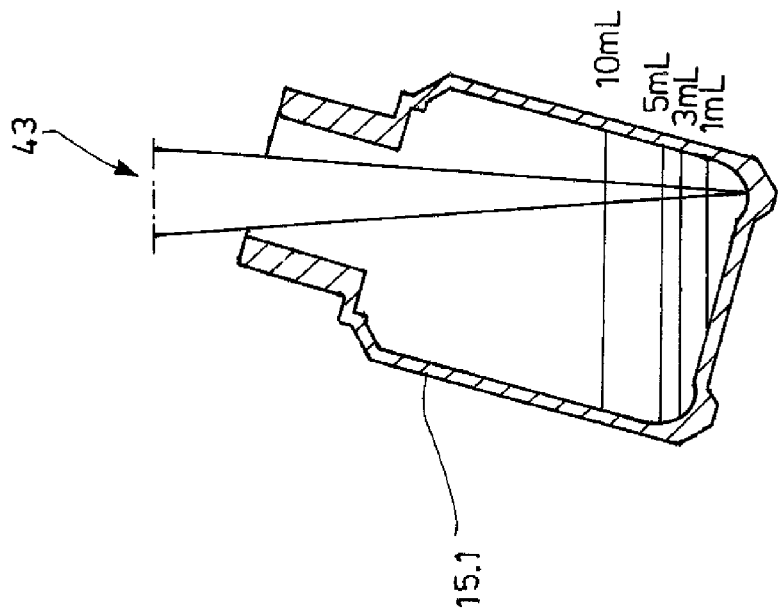
FIG. 22 shows a vertical section of the immersion of the pipette tip in another inclined vessel.

FIG. 22 shows the vessel 15.2 when fluid is being removed by means of a pipette tip 43. Due to the inclination of the vessel 15.2, only the slightest amount of fluid remains in the vessel in this case as well.

FIG. 23 shows the vessel 15.4 when reagent is being removed. In this case, more residue remains since the vessel 15.4 is aligned nearly vertically, and the vessel bottom bulges upward. The vessel 15.4 is therefore intended for accommodating more cost-effective reagents.

Finally, FIG. 24 shows that the vessel 15.3 can almost be emptied completely despite the vertical alignment since the vessel bottom bulges downward and the remaining amount of fluid collects in the center of the vessel bottom. The vessel 15.3 is intended especially for expensive reagents of which only very small amounts are required, and a pipette tip 43 would not fit through the vessel opening if the vessel 15.3 was inclined towards the vertical.

Figure 25:
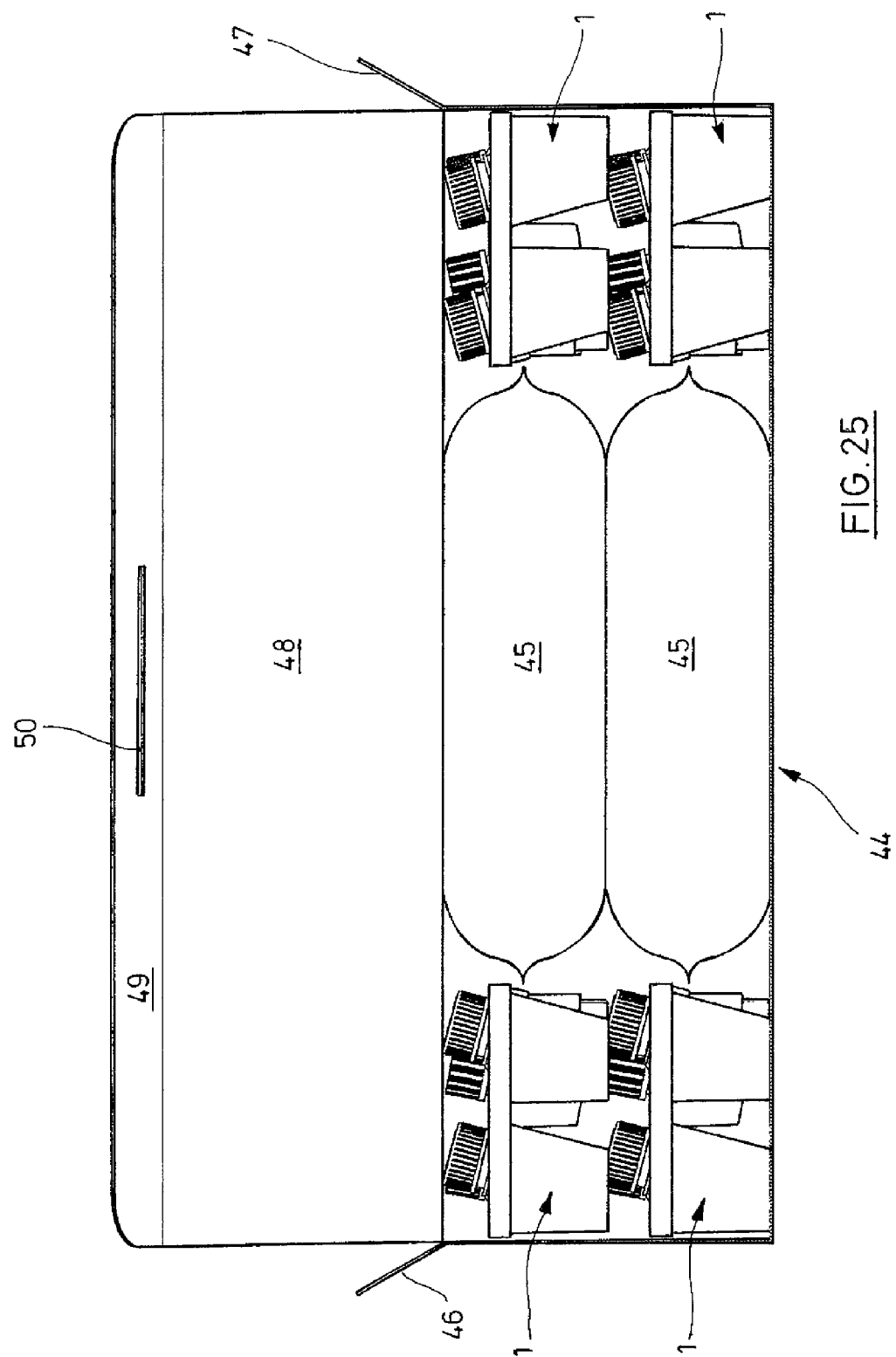
FIG. 25 shows a vertical section of two stacks of main bodies equipped with vessels having two bags containing empty reaction vessels therebetween in an external packaging made of cardboard with an open cover.
Figure 26:
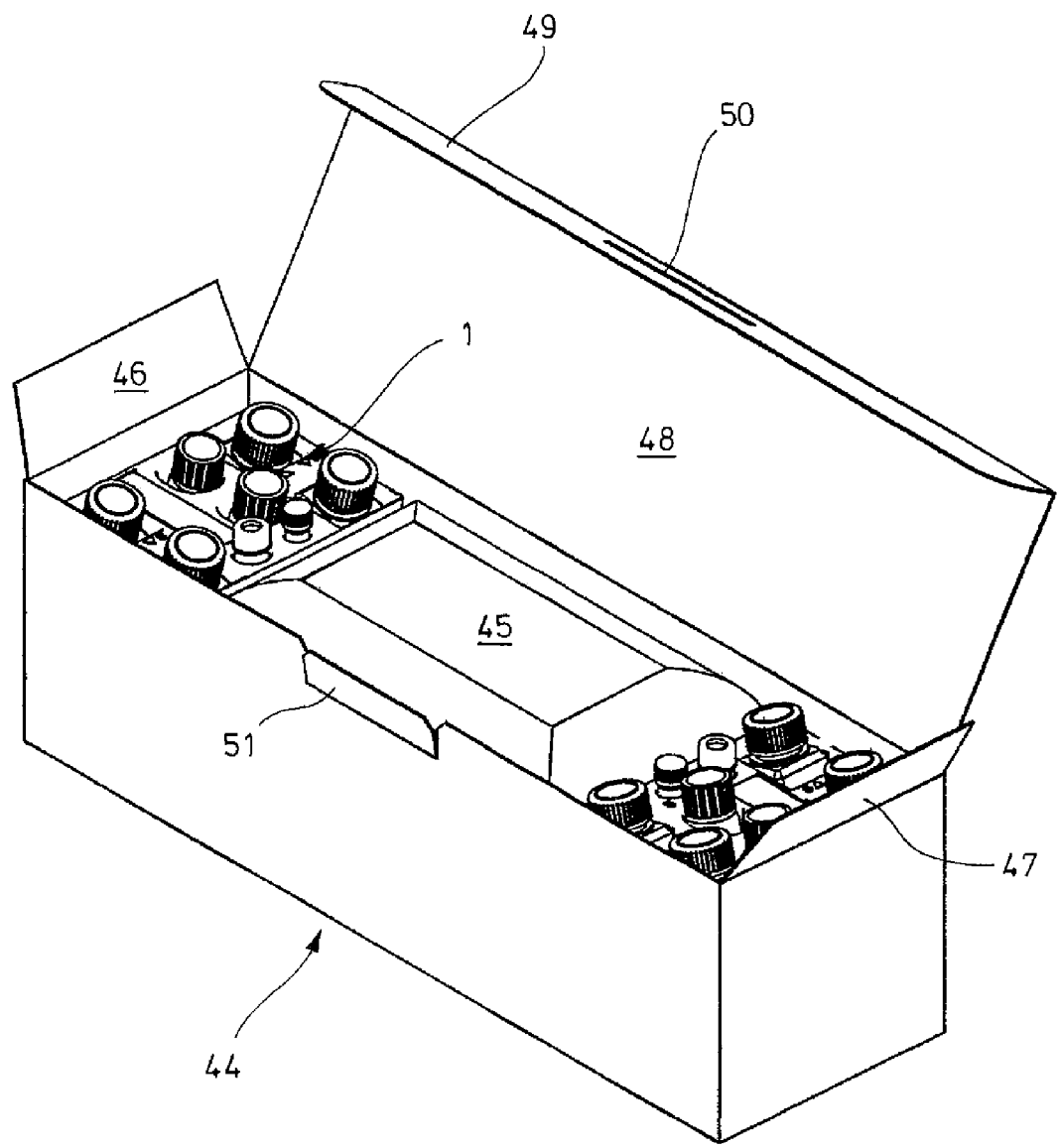
FIG. 26 shows a perspective view of the arrangement from FIG. 25 at an angle from above and from the side.

According to FIGS. 25 and 26, two stacked main bodies 1 with filled vessels 15 therein are inserted into a cuboidal folding box 44 made of cardboard. Plastic bags 45 filled with empty reaction vessels are arranged between the two stacks. The folding box 44 has dust flaps 46, 47 at the two narrow top edges of walls, and it has a cover 48 on a long top edge of a wall. The cover 48 has a closing flap 49 with an insertion slot 50 for a locking flap 51. The locking flap 51 is formed at the top edge of an opposing wall of the folding box. After the dust flaps 46, 47 are swung down, the cover 48 can be swung closed. The closing flap 49 is inserted behind the opposing wall. Then the cover 48 can be secured in closed position after inserting the locking flap 51 into the insertion slot 50. Then the equipped storage elements 1 are put away protected against environmental influences.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

REFERENCE LIST

1 Main body
2 Top wall
3, 3.1 to 3.4 Containers
4, 4.1 to 4.4 Seat
5, 5.1 to 5.4 Bottom
5.11 to 5.13 Bottom section
5.31, 5.32 Bottom section
5.41, 5.42 Bottom section
6, 6.1 to 6.4 Side wall section
6.21 to 6.24 Side wall section
6.31 to 6.32 Side wall section
6.41 to 6.42 Side wall section
7, 7.1 to 7.4 Top opening
8, 8.1, 8.2 Footprint
9.1, 9.2 Step
10 Edging
11 Gap
12, 12.1 to 12.4 ID
13 Additional ID
14 Hole
15, 15.1 to 15.4 Vessel
16, 16.1 to 16.4 Vessel body
17, 17.1 to 17.4 Vessel cover
18a Label
19 Adapter
20 Bottom part
21 Top part
22, 23 Housing wall
24 to 27 Housing wall section
28 to 31 Edge area
32, 33 Additional housing wall
34 Carrier
35 to 38.1 Pin
39 Workplace
40 Automated laboratory system
41 Positioning means
42 Additional positioning means
43 Pipette tip
44 Folding box
45 Plastic bag
46, 47 Dust flap
48 Cover
49 Closing flap
50 Insertion slot
51 Locking flap

The invention claimed is:

1. A kit comprising a carrier (34) and vessels (15) arranged on the carrier (34), wherein different reagents are contained in different vessels (15), the vessels (15) are arranged with an openable closing device (17) on top of the carrier (34), the carrier (34) has a footprint (8) on the bottom side for being placed on a base, and the carrier (34) has bottom positioning means (41) for being positioned on at least one workplace (39) of an automated laboratory system (40) for microtiter plates according to the SBS standard, the vessels (15) with the openable closing device (17) are arranged on top of the carrier (34) and are held by retaining means (4) of the carrier, wherein the retaining means (4) hold at least one vessel (15) when the footprint (8) of the carrier (34) is arranged on the base aligned inclined towards the vertical.

2. The kit according to claim 1, wherein the positioning means (41) are outer edges of a base of the carrier (3) that have dimensions which correspond to the dimensions of at least one workplace (39) of an automated laboratory system (40) for a microtiter plate according to the SBS standard.

3. The kit according to claim 1, wherein the retaining means comprise at least one seat (4) of the carrier (34) in which a vessel (15) is arranged, wherein the vessel (15) abuts at least one guide surface (5.12, 5.13, 5.2, 6.11, 6.21) in at least one seat (4) that is aligned so that the vessel (15) is inclined towards the vertical when the footprint (8) of the carrier (34) is arranged on a horizontal base.

4. The kit according to claim 3, wherein the guide surface (5.12, 5.13, 5.2) is a bottom of the seat that is inclined at an angle towards the footprint (8) and on which the vessel (15) rests, and/or wherein the guide surface (6.11, 6.21) is a side wall of the seat (4).

5. The kit according to claim 4, wherein the vessel (15) abuts a top opening (7) of the seat (4) with the inclined bottom (5) on one side at a side wall section (6.11, 6.21) of the seat (4) and not on the opposite side so that a viewer can observe an ID on the side of the vessel (15) through the top opening (7) in the seat.

6. The kit according to claim 5, wherein the cross-section of the seat (4) with the inclined bottom (5.12, 5.13, 5.2) expands upwards to the top opening (7) in the seat (4).

7. The kit according to claim 5, wherein the carrier (34) has a top wall (2) and containers (3) that project downward from the top wall (2), wherein the top openings (7) are formed in the top wall (2), and the seats (4) are formed in the containers (3).

8. The kit according to claim 5, wherein the footprint (8) of the main body (1) is formed on the bottom side of the bottoms (5) of the seats.

9. The kit according to claim 8, wherein the containers (3) project downward from the top wall (2) to different lengths, and the bottom side of the bottoms (5) of the containers (3) projecting furthest downward form the footprint (8.1) of the main body (1).

10. The kit according to claim 9, wherein the seat (4) with the inclined bottom (5) has two inclined bottom sections (5.12, 5.13) at a distance from each other, and a bottom section (5.11) therebetween that with the bottom side forms a section of the footprint (8.1) of the main body (1).

11. The kit according to claim 1, wherein the carrier (34) comprises a main body (1) carrying the vessels (15) and an adapter (19) holding the main body (1) with the footprint (8.2) on the bottom side, or wherein the carrier is a main body (1) carrying the vessels (15) with the footprint (8.1) on the bottom side.

12. The kit according to claim 11, wherein the adapter (19) has a frame with the footprint (8.3) on the bottom side of a bottom part (20) and a top part (21) that protrudes laterally above the bottom part (20) to receive the main body (1), and/or wherein the main body (1) has a bottom part with the footprint (8.2) on the bottom side and a top part (21) that protrudes laterally above the bottom part (20) to receive the vessels (15).

13. The kit according to claim 12, wherein the adapter (19) has two flat, opposing housing walls (22, 23) that in each case extend over the entire height of the bottom part (20) and top part (21), and wherein the adapter (19) in each case has two housing wall sections (24 to 27) aligned perpendicular to the opposing side wall (23, 22) in the region of the bottom part (20) at the two edges of the side walls (22, 23), and in the region of the top part (21), the two opposing side walls (22, 23) are connected to each other at their side edges by additional housing walls (32, 33) while projecting outward above the angled housing wall sections (24 to 27).

14. The kit according to claim 1, wherein the vessels (15) have IDs on a vessel body (16) and/or on a vessel cover (17), and corresponding IDs (12) are arranged on a top wall (2) of the carrier (34) next to top openings (7) of the seats (4) formed therein.

15. The kit according to claim 1, wherein a top wall (2) of the carrier (34) has at least one additional ID (13) that can be scanned by means of a sensor, and/or at least one surface for writing and/or a label (18).

16. The kit according to claim 1, wherein the carrier (34) is shaped in a complementary manner on the bottom side and on the top side with and without vessels (15) arranged thereupon such that a plurality of carriers (34) can be stacked upon each other with and without vessels (15) arranged thereupon.

17. The kit according to claim 1, wherein the carrier (34) is provided with a cover.

18. The kit according to claim 1, comprising an external packaging (42) in which at least one carrier (34) is arranged with vessels (15) arranged thereupon with or without covers.

19. The kit according to claim 18, comprising at least one stack of carriers (34) with vessels (15) arranged thereupon and/or a bag (45) with reaction vessels contained therein.

20. The kit according to claim 1, wherein the main body (1) is manufactured from at least one injection-molded plastic, or at least one plastic and/or another material that is deep-drawn or mechanically produced, and/or wherein the vessels (15) are made of at least one injection-molded plastic and/or blow-molded and/or are made of glass, and/or are made of at least one deep-drawn plastic and/or another material, and/or wherein the adapter (19) is made of at least one injection-molded plastic, or at least one plastic or another material that is deep-drawn or mechanically produced, and/or wherein the cover is made of at least one injection-molded plastic or at least one deep-drawn or mechanically produced plastic or another material, and/or wherein the external packaging (44) is a folding box made of cardboard and/or corrugated cardboard.

21. A carrier for a kit with vessels according to claim 1, wherein the carrier comprises the following elements:
  (a) a footprint (8) on the bottom side for being placed on a base;
  (b) positioning means (41) on its bottom side for being positioned on at least one workplace (39) of an automated laboratory system (40) for microtiter plates according to the SBS standard; and
  (b) retaining means (4) for holding vessels on the top side, wherein the retaining means (4) hold at least one vessel

(15) when the footprint (8) of the carrier (34) is arranged on the base and aligned inclined towards the vertical.

* * * * *